(12) United States Patent
Nair et al.

(10) Patent No.: US 11,964,279 B2
(45) Date of Patent: Apr. 23, 2024

(54) SAMPLE PREPARATION CARTRIDGES AND APPARATUSES

(71) Applicant: LexaGene, Inc., Beverly, MA (US)

(72) Inventors: Manojkumar M. Nair, Burlington, MA (US); John Frederick Regan, Boxford, MA (US)

(73) Assignee: LexaGene, Inc., Beverly, MA (US)

( * ) Notice: Subject to any disclaimer, the term of this patent is extended or adjusted under 35 U.S.C. 154(b) by 277 days.

(21) Appl. No.: 17/626,885

(22) PCT Filed: Jul. 14, 2020

(86) PCT No.: PCT/US2020/041875
§ 371 (c)(1),
(2) Date: Jan. 13, 2022

(87) PCT Pub. No.: WO2021/011512
PCT Pub. Date: Jan. 21, 2021

(65) Prior Publication Data
US 2022/0258162 A1 Aug. 18, 2022

Related U.S. Application Data

(60) Provisional application No. 62/874,212, filed on Jul. 15, 2019.

(51) Int. Cl.
*B01L 3/00* (2006.01)
*C12N 1/06* (2006.01)
(Continued)

(52) U.S. Cl.
CPC .......... *B01L 3/502753* (2013.01); *C12N 1/06* (2013.01); *C12N 15/1017* (2013.01);
(Continued)

(58) Field of Classification Search
CPC ....... B01L 3/502753; B01L 2200/0605; B01L 2300/0681; B01L 2400/0487;
(Continued)

(56) References Cited

U.S. PATENT DOCUMENTS 6,111,096 A 8/2000 Laugharn, Jr. et al.
6,153,104 A * 11/2000 Robertson ........... B01L 3/50255
210/406
(Continued)

FOREIGN PATENT DOCUMENTS

WO WO 2000/072970 A1 12/2000
WO WO 2015/073999 A1 5/2015
(Continued)

OTHER PUBLICATIONS

Extended European Search Report dated Jul. 13, 2023 for European Application No. 20840066.3.
(Continued)

*Primary Examiner* — Suman K Nath
(74) *Attorney, Agent, or Firm* — Wolf, Greenfield & Sacks, P.C.

(57) ABSTRACT

The invention includes sample preparation cartridges and apparatuses. The invention provides means for lysing and optionally selectively capturing at least one compound in a sample to purify, concentrate, and/or select for the at least one compound. The invention can be used in conjunction with a sample processing instrument to create a fully-automated or near-fully-automated sample workflow.

18 Claims, 8 Drawing Sheets

(51) Int. Cl.
*C12N 15/10* (2006.01)
*G01N 33/543* (2006.01)
*G01N 35/00* (2006.01)
*G01N 35/10* (2006.01)

(52) U.S. Cl.
CPC .................. *G01N 33/54326* (2013.01); *B01L 2200/0605* (2013.01); *B01L 2300/0681* (2013.01); *B01L 2400/0487* (2013.01); *B01L 2400/0622* (2013.01); *G01N 2035/00564* (2013.01); *G01N 2035/1032* (2013.01)

(58) Field of Classification Search
CPC .............. B01L 2400/0622; C12N 1/06; C12N 15/1017; G01N 33/54326; G01N 2035/00564; G01N 2035/1032; G01N 2035/00465; C12M 47/06
See application file for complete search history.

(56) References Cited

U.S. PATENT DOCUMENTS

| | | |
|---|---|---|
| 6,852,284 B1 | 2/2005 | Holl et al. |
| 9,144,799 B2 * | 9/2015 | Rose .................. B03C 5/026 |
| 9,555,411 B2 | 1/2017 | Kiani et al. |
| 9,789,481 B2 | 10/2017 | Petersen et al. |
| 9,816,135 B2 | 11/2017 | Edwards et al. |
| 9,855,554 B2 | 1/2018 | Ingber et al. |
| 9,861,720 B2 | 1/2018 | Dodd et al. |
| 10,386,377 B2 | 8/2019 | Kolb et al. |
| 2002/0197631 A1 | 12/2002 | Lawrence et al. |
| 2010/0003683 A1 | 1/2010 | Sarofim et al. |
| 2010/0021910 A1 * | 1/2010 | Cao .......................... G01N 1/34 435/270 |
| 2014/0179909 A1 | 6/2014 | O'Halloran et al. |
| 2015/0203806 A1 | 7/2015 | Yager et al. |
| 2015/0307826 A1 | 10/2015 | Dorrer et al. |
| 2015/0368634 A1 | 12/2015 | Dyer et al. |
| 2017/0088880 A1 * | 3/2017 | Brettschneider ..... C12Q 1/6806 |
| 2019/0136226 A1 | 5/2019 | Swenson et al. |
| 2023/0226546 A1 | 7/2023 | Nair et al. |

FOREIGN PATENT DOCUMENTS

| | | |
|---|---|---|
| WO | WO 2015/172255 A1 | 11/2015 |
| WO | WO 2015/179098 A1 | 11/2015 |
| WO | WO 2018/232167 A1 | 12/2018 |

OTHER PUBLICATIONS

U.S. Appl. No. 17/910,523, filed Sep. 9, 2022, Nair et al.
EP 20840066.3, Jul. 13, 2023, Extended European Search Report.
International Search Report and Written Opinion dated Oct. 14, 2020 for International Application No. PCT/US2020/041875.
International Preliminary Report on Patentability dated Jan. 27, 2022 for International Application No. PCT/US2020/041875.
International Search Report and Written Opinion dated May 19, 2021 for International Application No. PCT/US2021/020580.
International Search Report and Written Opinion dated Sep. 15, 2021 for International Application No. PCT/US2021/020580.
PCT/US2020/041875, Oct. 14, 2020, International Search Report and Written Opinion.
PCT/US2020/041875, Jan. 27, 2022, International Preliminary Report on Patentability.
PCT/US2021/020580, May 19, 2021, International Search Report and Written Opinion.
PCT/US2021/020580, Sep. 15, 2021, International Search Report and Written Opinion.

* cited by examiner

SAMPLE PREPARATION CARTRIDGES AND APPARATUSES

CROSS-REFERENCE TO RELATED APPLICATIONS

This application is a national stage filing under 35 U.S.C. § 371 of International Patent Application No. PCT/US2020/041875, filed Jul. 14, 2020, which claims the benefit of U.S. Provisional Patent Application No. 62/874,212 filed Jul. 15, 2019. The entire contents of these applications are incorporated herein by reference in their entireties.

FEDERALLY SPONSORED RESEARCH OR DEVELOPMENT

Not applicable.

TECHNICAL FIELD

The invention generally relates to sample preparation. The invention more specifically relates to sample preparation of samples comprising nucleic acids.

BACKGROUND

Many sample preparation methods are manual or semi-automated and therefore require labor that can be costly, introduce contamination problems, and lead to preparation errors. In addition, some samples need to be grown and/or enriched to detectable levels of target compounds prior to sample preparation. In addition, quality control sampling time is critical for food safety testing. Fresh food products must arrive to the seller (or reseller) quickly, but current quality control culture-based methods and protocols require 24 to 48 hours to confirm that the food products are pathogen-free. The ability to confirm that fresh food products are safe prior to shipping can extend shelf-life and reduce costs.

Thus, there is a need for sample preparation cartridges and apparatuses that overcome the aforementioned problems and limitations.

SUMMARY

The invention includes sample preparation cartridges and apparatuses. The invention provides means for lysing and optionally selectively capturing at least one compound in a sample to purify, concentrate, and/or select for the at least one compound.

The invention can be used in conjunction with a sample processing instrument to create a fully-automated or near-fully-automated sample workflow. When used in conjunction with a sample processing instrument, the invention allows for the detection of low copy numbers of target pathogens and the ability to determine whether nucleic acids in a sample are from viable (living) or non-viable (dead) organisms. One application of the invention is the detection and quantification of food-borne pathogens. For example, when used in conjunction with a sample processing instrument, the invention allows for the the detection of *Salmonella* species, *Listeria* species, or Shiga-toxigenic *Escherichia coli* on food matrix samples, for example meat or produce, and environmental samples, for example a swab or sponge.

The invention also provides means for sample growth and/or enrichment, during an automated sample extraction time series as well as automated sample metering.

Unless otherwise defined, all terms used herein have the same meaning as commonly understood by a person having ordinary skill in the art to which the invention pertains. All publications, patent applications, patents, and other references mentioned herein and/or listed in the Application Data Sheet are hereby incorporated by reference in their entirety. In case of conflict, the specification will control. When a range of values is provided, the range includes the end values.

The materials, methods, components, features, embodiments, examples, and drawings disclosed herein are illustrative only and not intended to be limiting.

DESCRIPTION OF DRAWINGS

The invention is best understood from the following detailed description when read in connection with the drawings disclosed herein, with similar elements having the same reference numbers. When a plurality (at least two) of similar elements are present, a single reference number may be assigned to the plurality of similar elements with a small letter designation referring to at least one specific similar element. When referring to the similar elements collectively or to a non-specific similar element, the small letter designation may be dropped. The various features of the drawings may not be drawn to scale and may be arbitrarily expanded or reduced for clarity. Included in the drawings are the following figures.

DETAILED DESCRIPTION

Figure 1:
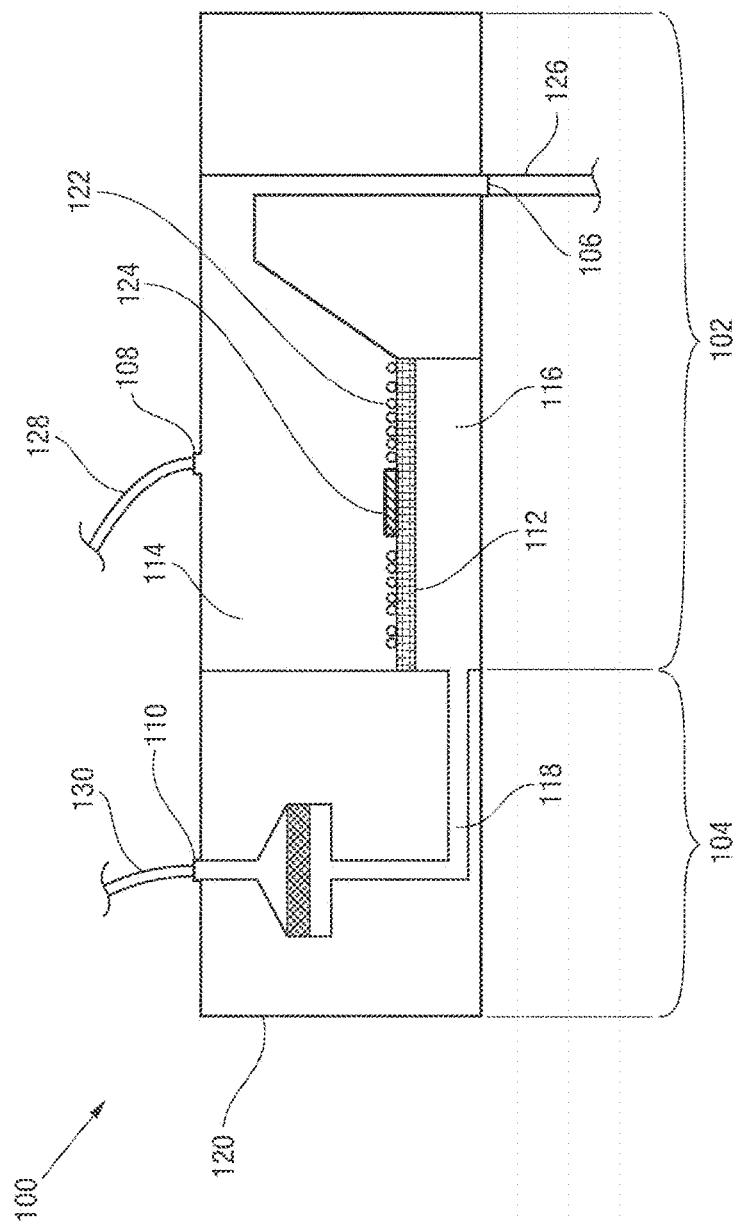
FIG. 1 is a diagram depicting a sample preparation cartridge in accordance with aspects of the invention.

FIG. 1 is a diagram depicting a sample preparation cartridge in accordance with aspects of the invention. The sample preparation cartridge 100 comprises a lysis chamber 102 and a nucleic acid capture chamber 104. The lysis chamber 102 comprises a first lysis chamber port 106 and a second lysis chamber port 108, both in fluidic connectivity with the lysis chamber 102. The nucleic acid capture chamber 104 comprises a nucleic acid capture chamber port 110 in fluidic connectivity with the nucleic acid capture chamber 104. The lysis chamber 102 further comprises a filter 112 that partitions the lysis chamber 102 into a first lysis chamber section 114 and a second lysis chamber section 116. The nucleic acid capture chamber 104 further comprises a fluidic channel 118 in fluidic connectivity with the second lysis chamber section 116 and the nucleic acid capture chamber port 110. The nucleic acid chamber port 110 further comprises a nucleic acid binding unit 120. In this diagram, the lysis chamber 102 further comprises beads 122 and a moveable magnetic bar 124 in the first lysis chamber section 114. The first lysis chamber port 106 is capable of establishing fluidic connectivity with a sample comprising nucleic acids (not depicted) via a tubing 126. The second lysis chamber port 108 is capable of establishing fluidic connectivity with at least one fluidic movement source (not depicted), for example at least one pump, via a tubing 128. The nucleic acid capture chamber port is capable of establishing fluidic connectivity with at least one fluidic movement source (not depicted), for example at least one pump, via a tubing 130.

In FIG. 1, a sample comprising nucleic acids (not depicted) enters the first lysis chamber section 114 of the sample preparation cartridge 100 via the tubing 126. In this embodiment, the sample is lysed in the first lysis chamber section by the lysis beads 122. A magnetic field device (not depicted) generates a magnetic field to move the moveable magnetic bar 124 and thereby move the lysis beads 122 to mechanically lyse the sample. Some of the lysed material (including nucleic acids) is able to cross the filter 112 and enter the second lysis chamber section 116. The sample in the second lysis chamber section 116 then enters the fluidic channel 118 and nucleic acids are captured by the nucleic acid binding unit 120. An elution buffer (not depicted) is used to release the nucleic acids from the nucleic acid binding unit 120, and the nucleic acids exit the sample preparation cartridge via the tubing 130.

Figure 2:
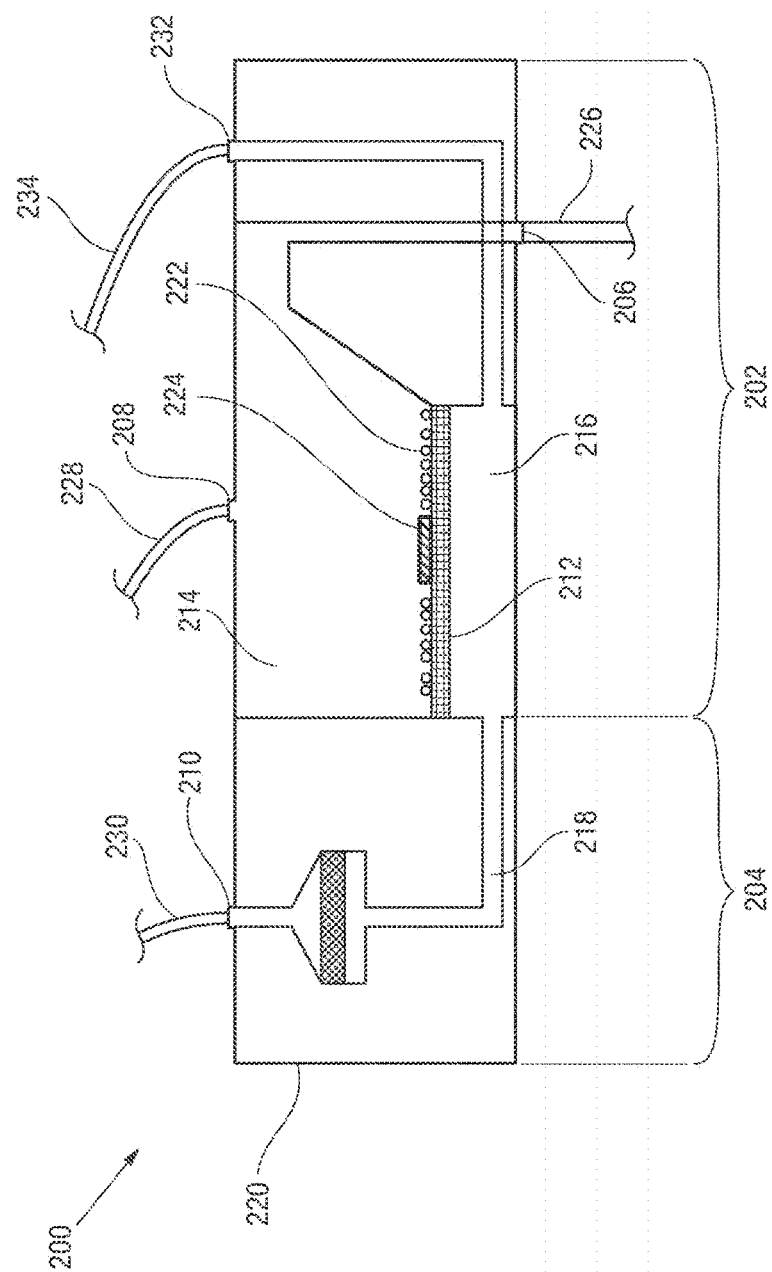
FIG. 2 is a diagram depicting a sample preparation cartridge in accordance with aspects of the invention.

FIG. 2 is a diagram depicting a sample preparation cartridge in accordance with aspects of the invention. The sample preparation cartridge 200 comprises a lysis chamber 202 and a nucleic acid capture chamber 204. The lysis chamber 202 comprises a first lysis chamber port 206 and a second lysis chamber port 208, both in fluidic connectivity with the lysis chamber 202. The nucleic acid capture chamber 204 comprises a nucleic acid capture chamber port 210 in fluidic connectivity with the nucleic acid capture chamber 204. The lysis chamber 202 further comprises a filter 212 that partitions the lysis chamber 202 into a first lysis chamber section 214 and a second lysis chamber section 216. The nucleic acid capture chamber 204 further comprises a fluidic channel 218 in fluidic connectivity with the second lysis chamber section 216 and the nucleic acid capture chamber port 210. The nucleic acid capture chamber port 210 further comprises a nucleic acid binding unit 220. In this diagram, the lysis chamber 202 further comprises beads 222 and a moveable magnetic bar 224 in the first lysis chamber section 214. The first lysis chamber port 206 is capable of establishing fluidic connectivity with a sample comprising nucleic acids (not depicted) via a tubing 226. The second lysis chamber port 208 is capable of establishing fluidic connectivity with at least one fluidic movement source (not depicted), for example at least one pump, via a tubing 228. The nucleic acid capture chamber port is capable of establishing fluidic connectivity with at least one fluidic movement source (not depicted), for example at least one pump, via a tubing 230.

In FIG. 2, the sample preparation cartridge 200 is the same as the sample preparation cartridge 100 except that sample preparation cartridge 200 further comprises a third lysis chamber port 232 in fluidic connectivity with the second lysis chamber section 216. The third lysis chamber port 232 is capable of establishing fluidic connectivity with at least one fluidic movement source (not depicted), for example at least one pump, via a tubing 234. The at least one fluidic movement source (not depicted) in fluidic connectivity with the second lysis chamber section 216 is capable of removing fluid from the second lysis chamber section 216 via the tubing 234 as well as dispensing fluid to the second lysis chamber section 216 via the tubing 234.

Figure 3:
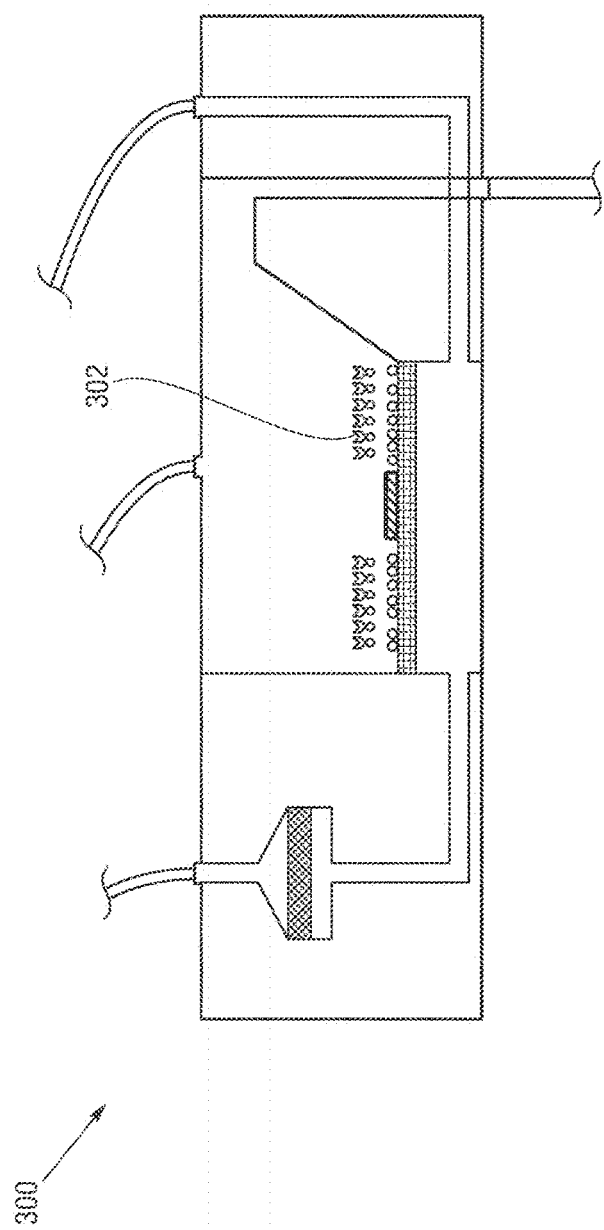
FIG. 3 is a diagram depicting a sample preparation cartridge in accordance with aspects of the invention.

FIG. 3 is a diagram depicting a sample preparation cartridge in accordance with aspects of the invention. The sample preparation cartridge 300 is the same as the sample preparation cartridge 200 except that sample preparation cartridge 300 further comprises selective capture beads 302 for selectively capturing at least one substance in the sample (not depicted). In this embodiment, the selective capture beads 302 are beads coated with a ligand such as an antibody, aptamer, polysaccharide, protein, and a combination thereof.

Figure 4:
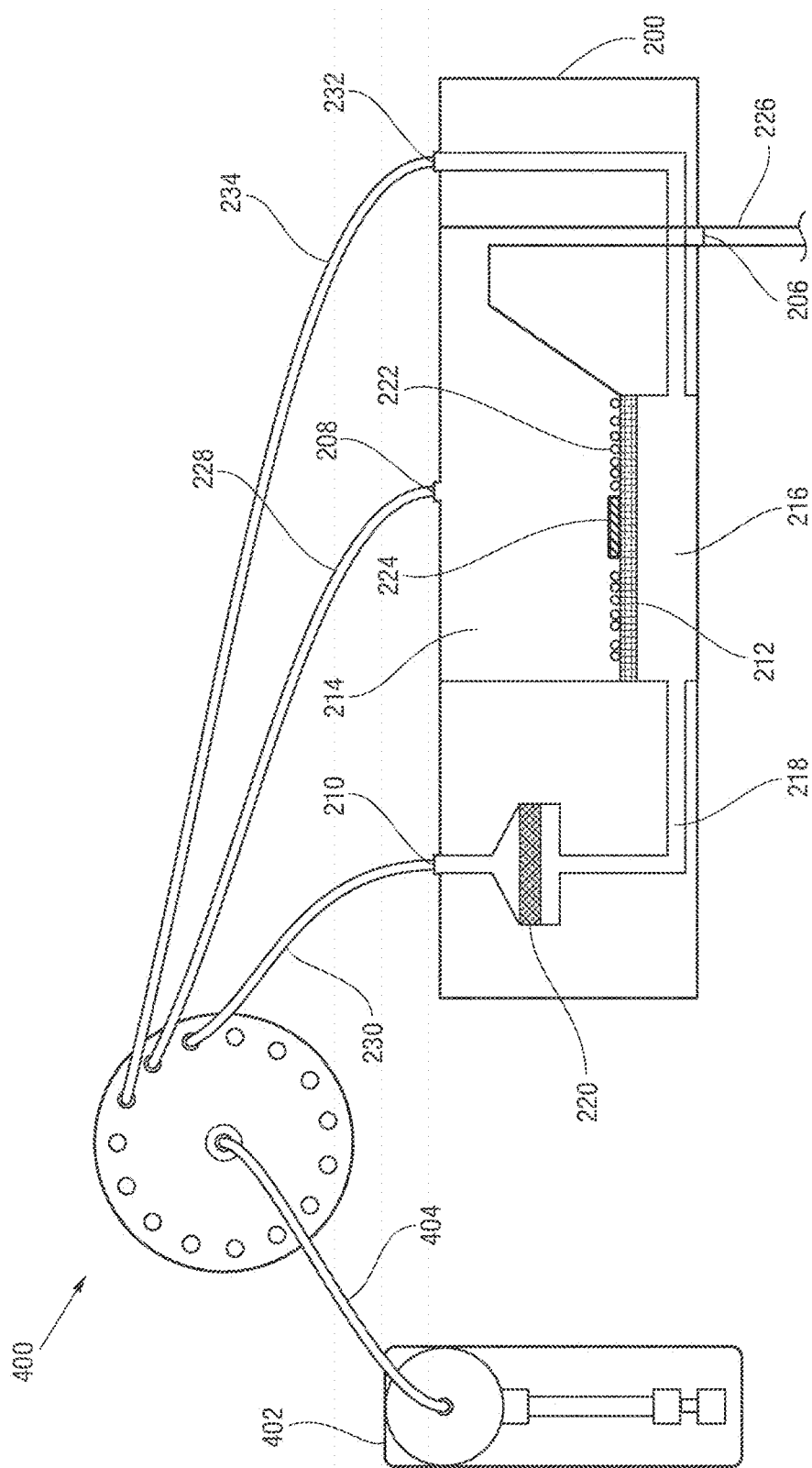
FIG. 4 is a diagram depicting a sample preparation cartridge in accordance with aspects of the invention.

FIG. 4 is a diagram depicting a sample preparation cartridge in accordance with aspects of the invention. The sample preparation cartridge 200 is in fluidic connectivity with a valve 400. More specifically, the second lysis chamber port 208 is in fluidic connectivity with the valve 400 via the tubing 228, the nucleic acid capture chamber port 210 is in fluidic connectivity with the valve 400 via the tubing 230, and the third lysis chamber port 232 is in fluidic connectivity with the valve 400 via the tubing 234. The valve 400 is in fluidic connectivity with a pump 402 via a tubing 404. The valve 400 can also be in fluidic connectivity with a sample processing instrument (not depicted).

In FIG. 4, a preferred method of using the sample preparation cartridge 200 is as follows: (1) close the capture chamber port 210 and the third lysis chamber port 232 at the valve 400, (2) aspirate through the second lysis chamber port 208 using the pump 402 to move a specific volume of a sample comprising nucleic acids (not depicted) to the first lysis chamber section 214 (filter 212 will prevent the sample from entering the second lysis chamber section 216), (3) close the capture chamber port 210 and the second lysis chamber port 208 at the valve 400, (4) aspirate through the third lysis chamber port 232 using the pump 402 to move the fluid portion of the sample through the third lysis chamber port 232 (particulates and cells in the sample that are larger than the pore size of the filter 212 will be retained on the filter 212), (5) close the capture chamber port 210 and the third lysis chamber port 232 at the valve 400, (6) flow lysis buffer (not depicted) into the first lysis chamber section 214 through the second lysis chamber port 208 using the valve 400 and pump 402, (7) move the moveable magnetic bar 224 using a magnetic field device (not depicted) to lyse the cells using the lysis buffer and colliding them with the moveable magnetic bar 224 and the the lysis beads 222 (to create lysate), (8) close the second lysis chamber port 208 and the third lysis chamber port 232 at the valve 400, (9) aspirate the lysate through the capture chamber port 210 to capture the nucleic acids in the lysate on the nucleic acid binding unit 220, (10) close the capture chamber port 210 and the the third lysis chamber port 232 at the valve 400, (11) flow wash buffer (not depicted) into the first lysis chamber section 214 through the second lysis chamber port 208 using the valve 400 and pump 402, (12) close the second lysis chamber port 208 and the third lysis chamber port 232 at the valve 400, (13) aspirate the wash buffer through the capture chamber port 210 using the pump 402 to wash the nucleic acids bound to the nucleic acid binding unit 220, (14) flow elution buffer (not depicted) into the fluidic channel 218 through the capture chamber port 210 using the valve 400 and pump 402 to contact the nucleic acid binding unit 220 and the bound nucleic acids (to release the nucleic acids from the nucleic acid binding unit 220), and (15) aspirate the elution buffer through the capture chamber port 210 for processing by a sample processing instrument (not depicted) in fluidic connectivity with the valve 400.

Figure 5:
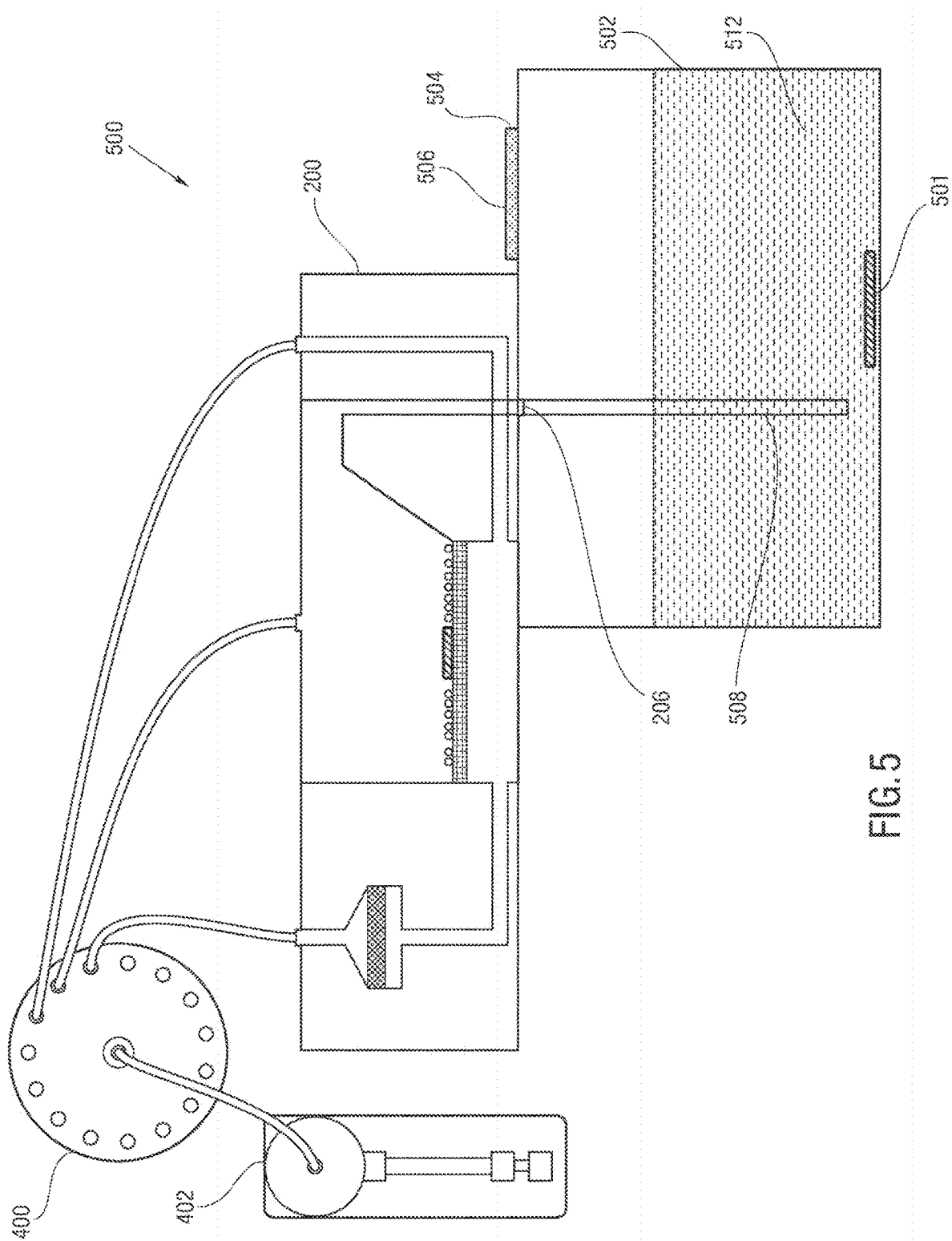
FIG. 5 is a diagram depicting a sample preparation apparatus in accordance with aspects of the invention.

FIG. 5 is a diagram depicting a sample preparation apparatus in accordance with aspects of the invention. The sample preparation apparatus 500 comprises the sample preparation cartridge 200, which is in fluidic connectivity with valve 400 and pump 402. The valve 400 can also be in fluidic connectivity with a sample processing instrument (not depicted). In addition, the sample preparation apparatus further comprises a sample container 502 in fluidic connectivity with the sample preparation cartridge 200 via the first lysis chamber port 206. In this embodiment, the sample container 502 comprises a sample container port 504, a sample container port cap 506, a tubing 508, a moveable magnetic bar 510, and a sample 512 comprising nucleic acids. Media (not depicted) can also be inserted into the sample container 502 via the sample container port 504.

In FIG. 5, the sample 512 (which can be inserted into the sample container via the sample container port 504) is mixed by the moveable magnetic bar 510. A magnetic field device (not depicted) generates a magnetic field to move the moveable magnetic bar 510 and thereby mix the sample 512. After the sample is mixed or while mixing is occurring, a portion of the sample 512 moves to the sample preparation cartridge 200 via the the tubing 508 where the portion of the sample 512 can be prepared by the sample preparation cartridge 200. If the valve 400 is also in fluidic connectivity with a sample processing instrument (not depicted), then the portion of the sample 512 can move to the sample processing instrument after it is prepared by the sample preparation cartridge 200.

Figure 6:
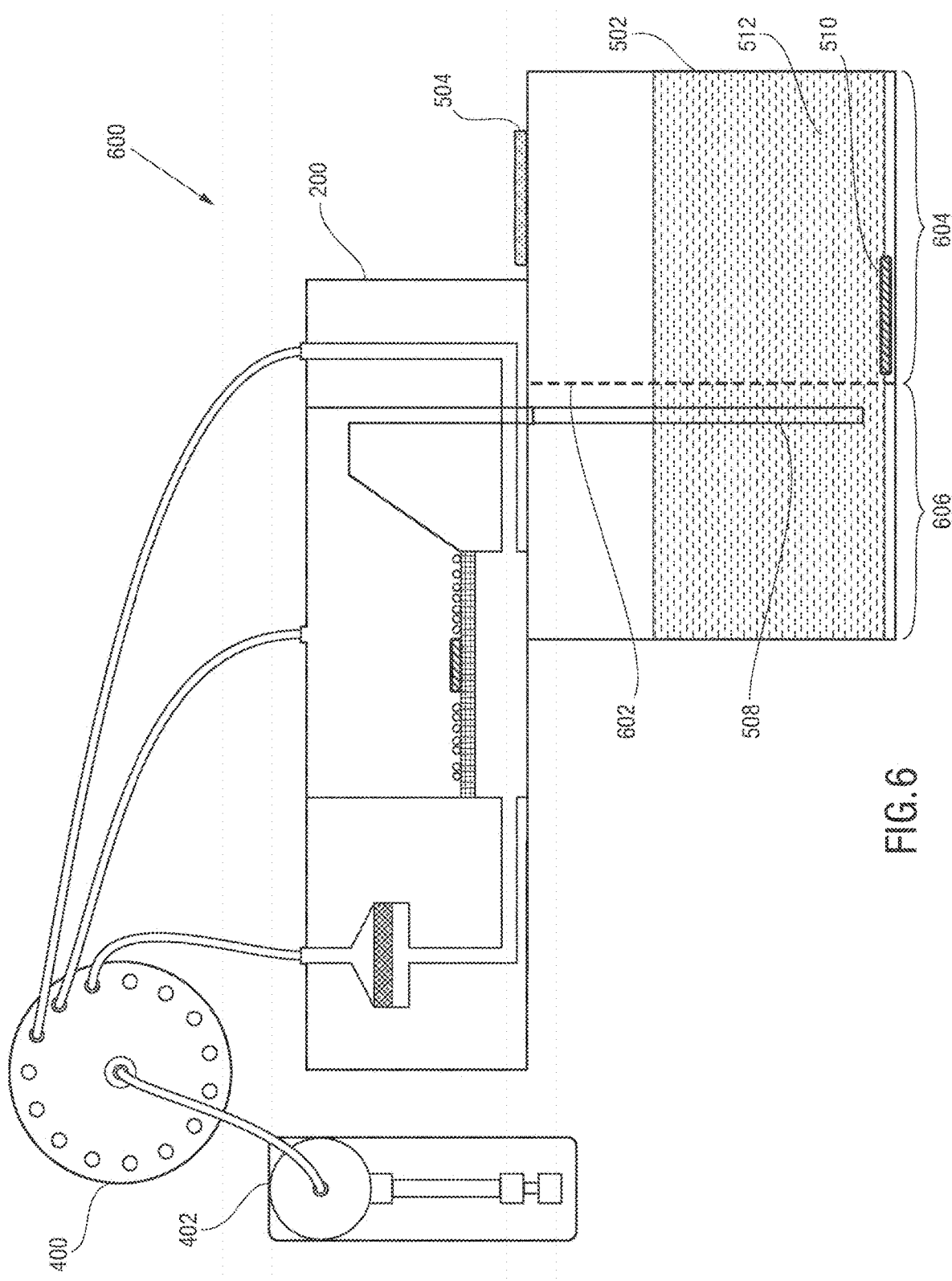
FIG. 6 is a diagram depicting a sample preparation apparatus in accordance with aspects of the invention.

FIG. 6 is a diagram depicting a sample preparation apparatus in accordance with aspects of the invention. The sample preparation apparatus 600 is the same as the sample preparation apparatus 500 except that the sample container 502 further comprises a semipermeable membrane 602 that partitions the sample container 502 into a first sample container section 604 and a second sample container section 606. In this embodiment, the sample container port 504 is in fluidic connectivity with the first sample container section 604, and therefore the sample 512 will be inserted into the first sample container section 604 via the sample container port 504. Some of the substances in the sample 512 will be able to cross the semipermeable membrane 602 and therefore move between the first sample container section 604 and the second sample container section 606, while other substances in the sample 512 will be unable to cross the semipermeable membrane 602 and therefore will only be present in the first sample container section 604.

In FIG. 6, the moveable magnetic bar 510, which is capable of being moved by an external magnetic field device (not depicted) outside the sample container 502, is capable of mixing the sample 512 and any media (not depicted) in the sample container 502. The mixing of the sample 512 by the moveable magnetic bar 510 will aid the separation of the substances in the sample 512. Only the substances of the sample 512 that are able to cross the semipermeable membrane 508 into the second sample container section 606 will be able to move to the sample preparation cartridge 200 via the the tubing 508.

Figure 7:
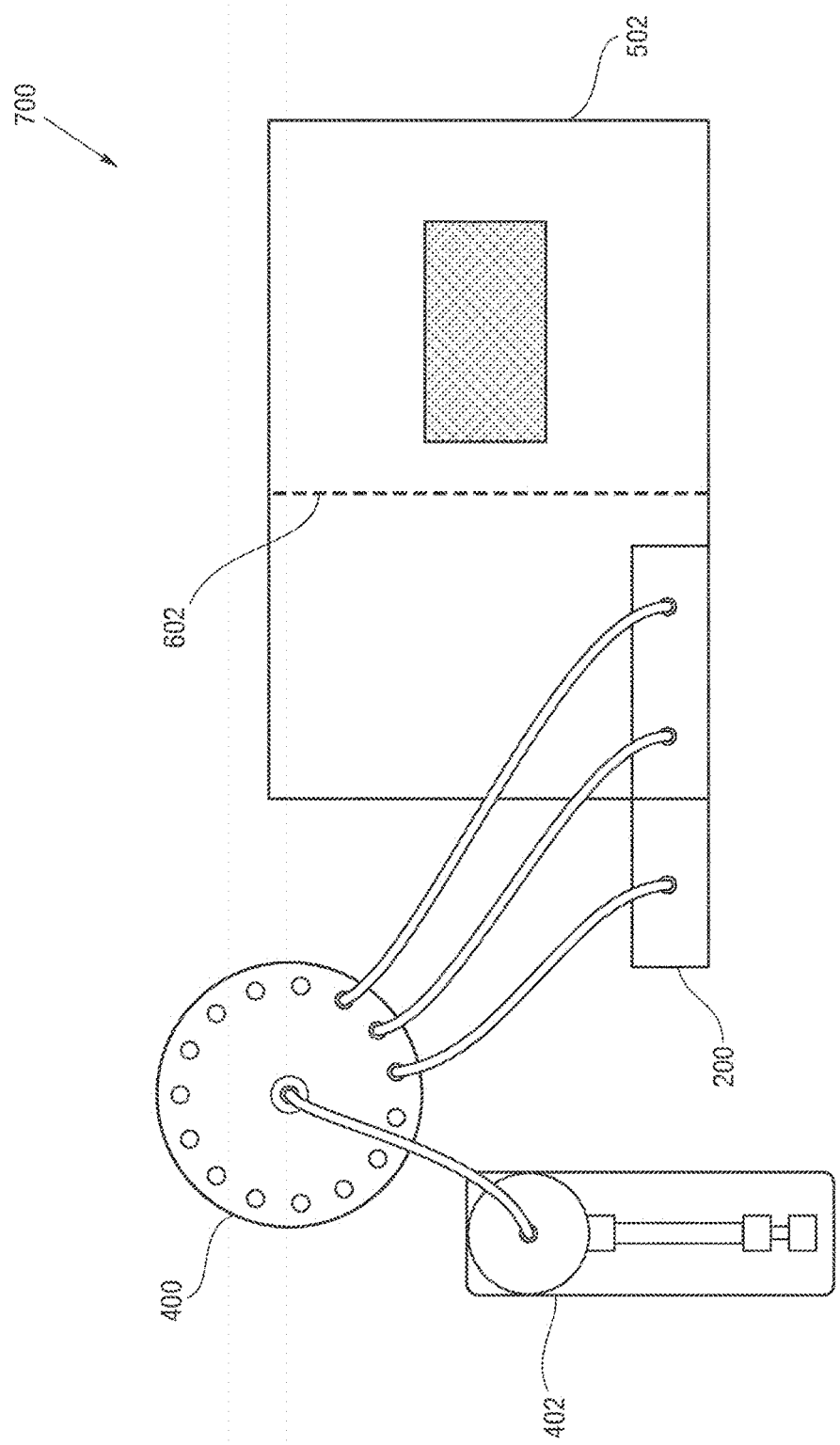
FIG. 7 is a diagram depicting a sample preparation apparatus in accordance with aspects of the invention.

FIG. 7 is a diagram depicting a sample preparation apparatus in accordance with aspects of the invention. The sample preparation apparatus 700 is the same as the sample preparation apparatus 600 except that the sample preparation cartridge 200 and the sample container 502 are shown in a top view.

Figure 8:
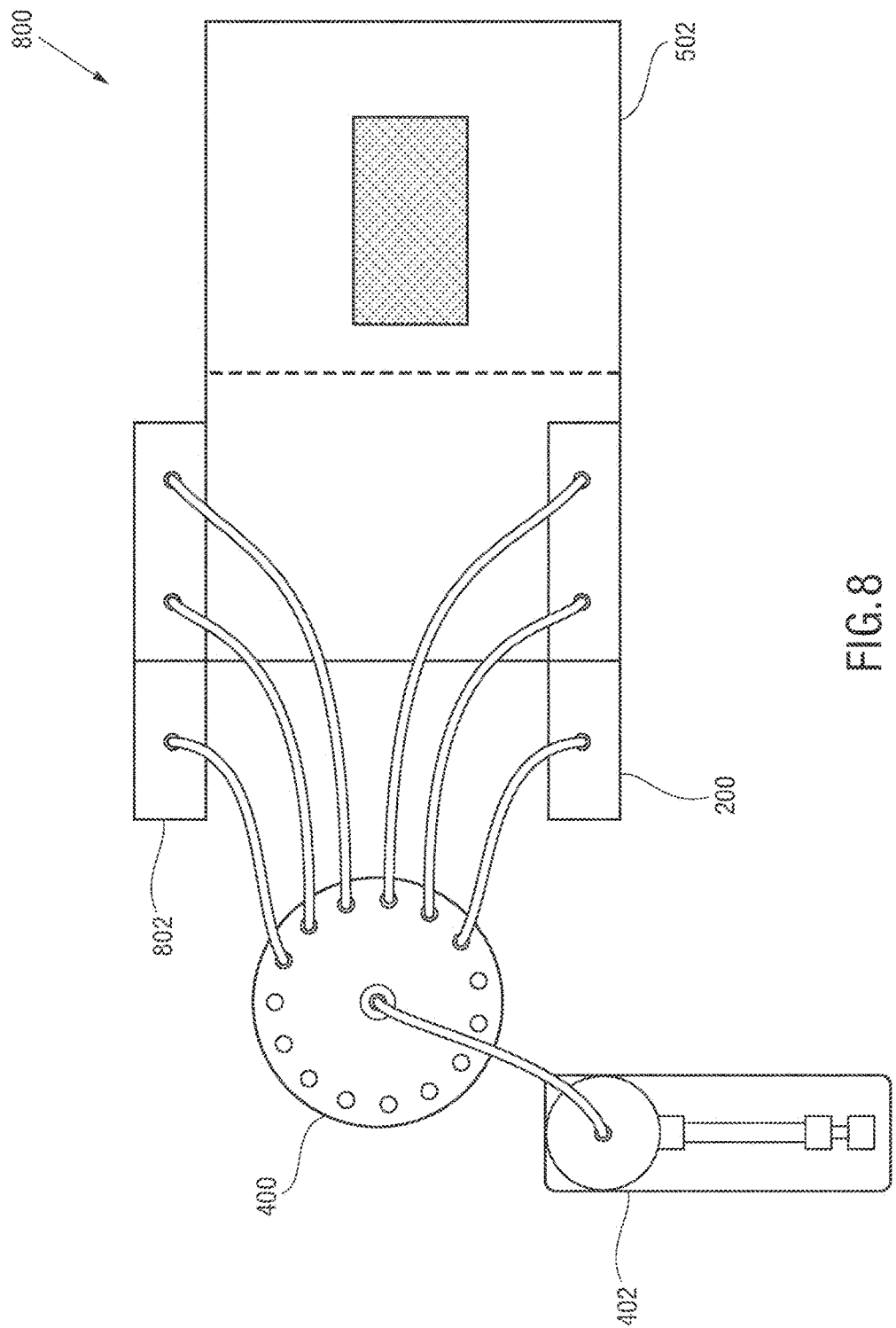
FIG. 8 is a diagram depicting a sample preparation apparatus in accordance with aspects of the invention.

FIG. 8 is a diagram depicting a sample preparation apparatus in accordance with aspects of the invention. The sample preparation apparatus 800 is the same as the sample preparation apparatus 700 except that a second sample preparation cartridge 802 is in fluidic connectivity with the sample container 502 and the valve 400. In this embodiment, the sample preparation cartridge 200 can prepare a portion of the sample (not depicted) in the sample container 502 at a first time point (t1) and the sample preparation cartridge 802 can prepare a portion of the sample in the sample container 502 at a second time point (t2), or vice versa. The valve 400 can be in fluidic connectivity with a sample processing instrument (not depicted) and thus allow for the automated preparing and processing of portions of the sample (not depicted) in the sample container 502 at different time points (t1 and t2).

In FIG. 8, a preferred method of using the sample preparation apparatus 800 is as follows: (1) for time point 1 (t1), use the sample preparation cartridge 200 in accordance with the preferred method described above for using the sample preparation cartridge 200 and (2) for time point 2 (t2), use the sample preparation cartridge 802 in accordance with the preferred method described above for using the sample preparation cartridge 200. A person skilled in the art will understand that additional sample preparation cartridges in fluidic connectivity with the sample container 502, the valve 400, and the pump 402 can be used for additional time points. For a sample preparation apparatus, the number of sample preparation cartridges the can be used with a sample container includes but is not limited to 1, 2, 3, 4, 5, 6, 7, 8, 9, 10, 11, 12, 13, 14, 15, 16, 17, 18, 19, 20 or more sample preparation cartridges.

For clarity, the invention is described under the following headings: "Sample Preparation Cartridge," "Lysis," "Selective Capture," "Nucleic Acid Capture," "Sample and Sample Container," "Metering of Fluids," "Sample Processing Instrument," and "Multiple Sample Preparation Cartridges."

Sample Preparation Cartridge

The invention includes cartridges for sample preparation. The sample preparation cartridges contain two chambers: a lysis chamber and a nucleic acid capture chamber. A fluid sample comprising nucleic acids enters the lysis chamber where the cells are lysed and the nucleic acids are released into the fluid. The nucleic acids are then transported to the nucleic acid capture chamber where the nucleic acids are captured on a nucleic acid binding unit. The nucleic acids are then released from the nucleic acid binding unit and enter a sample processing instrument in a more purified and concentrated state.

A sample preparation cartridge can be made of any rigid material including but not limited to metal and plastic and can be created by a variety of methods including molding, extrusion, and additive manufacturing (3D printing).

The invention also provides means for selectively capturing at least one component in a sample. Selective capture allows for the removal of non-targeted substances and thereby the output from the sample preparation cartridge can be a subset of the nucleic acids originally in a sample. For example, certain cells can be selectively captured prior to lysing using a ligand such as an antibody, aptamer, polysaccharide, protein, and a combination thereof.

The non-captured cells are removed and the lysis of the selectively captured cells releases only the nucleic acids from those cells ("selected nucleic acids"). The selected nucleic acids are then captured on the nucleic acid binding unit and then released into the sample processing instrument. Therefore, the nucleic acids that enter the sample processing instrument are purified, concentrated, and selected for.

A sample preparation cartridge (and a sample preparation apparatus) are preferably single-use disposable consumables to prevent contamination and potential exposure to samples comprising pathogens.

Lysis

The lysis of cells in a sample in the lysis chamber occurs prior to the capture of the nucleic acids on the nucleic acid binding unit in the nucleic acid capture chamber. The lysis can occur by any suitable means including but not limited to mechanical, chemical, biological, heat, and acoustic and a combination thereof.

Mechanical lysis involves breaking cells by colliding them with moveable structures. Such moveable structures include but are not limited to bars, beads, rings, plates, and any combination thereof. The moveable structures can be moved by any suitable means including but not limited to magnetism and stirring. If the moveable structures are magnetic, for example magnetic beads, then a magnetic field needs to be generated to move the magnetic moveable structures. For example, magnetic beads can be used to mechanically lyse cells in a sample by exposing the magnetic beads to a changing or moving magnetic field. The collisions between the magnetic beads and the cells causes the cell membranes to break. At least one moveable structure can be in the lysis chamber prior to the introduction of a sample, can be introduced along with the sample, or can be loaded into the lysis chamber after the cells have been introduced, or a combination thereof. In a preferred embodiment, the magnetic field is generated by a magnetic field device, for example an electromagnet, on the sample processing instrument. Moveable structures can also be moved by stirring, which can be generated by any suitable means including but not limited to a magnetic stirrer, for example a magnetic stir bar, or a mechanical stirrer (stirring device), for example a vortexer or propeller. For example, a magnetic stir bar can be used to cause the moveable structures, which can be magnetic or non-magnetic, to move and thereby collide with and break cells that are present in the sample. If a magnetic field is used, either to move magnetic structures directly or to control a magnetic stirrer, at least one magnetic field device needs to be on the sample preparation cartridge or a part of the sample processing instrument. If at least one magnetic field device is a part of the sample processing instrument, then the sample preparation cartridge needs to be brought into close enough proximity with the at least one magnetic field device to allow for magnetic connectivity between the at least one magnetic field device and the magnetic structures and/or magnetic stirrer.

Chemical lysis uses at least one chemical compound to break cell membranes. Suitable chemical compounds include but are not limited to detergents, for example sodium dodecyl sulfate (SDS) and cetyl trimethyl ammonium bromide (CTAB), and chaotropes, for example guadinine salts (Herzer). At least one chemical lysing compound can be in the lysis chamber prior to the introduction of a sample, can be introduced along with the sample, or can be loaded into the lysis chamber after the cells have been introduced, or a combination thereof.

Biological lysis uses at least one biological compound to break cell membranes. Suitable biological compounds include but are not limited to enzymes for example proteases, lyticases, lysozymes, and labiase. At least one biological lysing compound can be in the lysis chamber prior to the introduction of a sample, can be introduced along with the sample, or can be loaded into the lysis chamber after the cells have been introduced, or a combination thereof.

Heat lysis uses heat to break cell membranes. The cell membranes can be heated by any suitable means including conduction, convection, and/or radiation. Heat is generated by a heating device, preferable an electric heating device such as an electric heating element or Peltier heater. The electric heating device can be attached to the sample preparation cartridge or can be on the sample processing instrument. If the electric heating device is part of the sample processing instrument, then the sample preparation cartridge needs to be brought into close enough proximity with the heating device to allow for sufficient heat transfer via convection, conduction, and/or radiation. Heat can also be generated by an exothermic chemical reaction. U.S. Published Patent Application No. 2006/0115873, hereby incorporated by reference in its entirety, discloses exothermic chemical reactions for cell lysis. In the case of an exothermic chemical reaction, the necessary reagents can be in the lysis chamber prior to the introduction of a sample, can be introduced along with the sample, or can be loaded into the lysis chamber after the cells have been introduced, or a combination thereof.

Acoustic lysis uses ultrasound (high frequency) energy waves to break cell membranes. An acoustic wave device (sonicator) can be on the sample preparation cartridge or, preferably, a part of the sample processing instrument. If an acoustic wave device is a part of the sample processing instrument, then the sample preparation cartridge needs to be brought into close enough proximity with the acoustic wave device to allow for sufficient acoustic exposure of cells in a sample. U.S. Pat. No. 9,096,823, hereby incorporated by reference in its entirety, discloses acoustic wave devices for cell lysis.

The lysis chamber comprises a filter that partitions the lysis chamber into a first lysis chamber section and a second lysis chamber section. The filter is comprised of suitable low-binding membrane materials including but not limited to cellulose acetate, polyethersulfone, polycarbonate, and a combination thereof. The pore size of the membrane is selected such that the pores will retain at least some substances of interest in the sample on and/or in the filter, while allowing the fluid to pass through along with smaller-sized particles when suitable pressure is applied.

Selective Capture

In addition to the lysis of cells in the lysis chamber, at least one compound in a sample can be selectively captured in the lysis chamber. Selective capture is used to isolate at least one compound in a sample from at least one other compound in a sample. Depending on the particular application, selective capture of at least one compound in a sample can occur before, after, and/or simultaneously with the lysis of cells in a sample. The selective capture can occur by any suitable means including but not limited to biological capture means. Examples of biological capture means include but are not limited to ligands such as an antibody, aptamer, polysaccharide, protein, and a combination thereof.

Antibody selective capture uses antibody-antigen binding to select for at least one antigen in a sample. The antigen is a cell or surface structures on or cellular components of a cell, and a specific antibody against the antigen is used to selectively capture the cell or its components. Aptamer selective capture uses specific oligonucleotides that can bind to a cell or surface structures on or cellular components of a cell to selectively capture the cell or its components. Polysaccharides selective capture uses specific polysaccharides that can bind to a cell or surface structures on or cellular components of a cell to selectively capture the cell or its components. Proteins selective capture uses specific proteins that can bind to a cell or surface structures on or cellular components of a cell to selectively capture the cell or its components. For example, a streptavidin-biotin complex. The biological capture means used depends on the particular application. For example, a suitably immobilized antibody against the somatic O157 antigen can be used to selectively capture cells of an *Escherichia coli* O157 strain from a sample containing different types of bacteria (Tu et al.).

Nucleic Acid Capture

After lysis (and optionally selective capture), nucleic acids from the sample are introduced into the nucleic acid capture chamber via a fluidic channel in fluidic connectivity with the lysis chamber. A fluidic channel is a defined flow path that includes but is not limited to a tubing (or multiple pieces of tubing), a microfluidic channel (or multiple microfluidic channels), and a combination thereof. The nucleic acids in the fluidic channel are exposed to a nucleic acid capture unit in the chamber. The nucleic acid capture unit can be any unit capable of capturing (and releasing) nucleic acids including but not limited to a frit, a filter, and a membrane. A nucleic acid capture unit can employ positively charged materials, such as silica under certain salt and pH conditions, and/or nucleic acids, such as oligonucleotides. The nucleic acid capture unit comprise of a frit, filter, membrane or a combination thereof. A frit can comprise a porous body made of materials including but not limited to glass, metal, ceramics, plastic or a combination thereof used to pack silica beads or particles in a column. A filter can comprise materials including but not limited to micro fibers of boro-silicate glass. A membrane can comprise microporous materials including but not limited to nylon, cellulose nitrate, polyvinylidene difluoride, or combinations thereof.

Sample and Sample Container

A sample preparation cartridge can be used in conjunction with a sample container. A sample container is a container that houses a sample that is to be introduced into the sample preparation cartridge. A sample container can be rigid, for example a box, or can be flexible, for example a bag or balloon. A sample container can be open, semi-open, or closed (sealed). Examples of a sample container include but are not limited to a box, bag, balloon, vial, tube, can, and jar.

A sample preparation container comprises at least one sample container port in fluidic connectivity with the lysis chamber of a sample preparation cartridge. At least one additional sample container port can be used for inserting the sample into and/or removing the sample from the sample container. A sample preparation container can also comprise a means for mixing. The means for mixing can be any suitable means including but not limited to a mechanical mixer (mixing device), for example a vortex mixer or propeller. The means for mixing can also be at least one magnetic moveable structure including but not limited to a bar, a bead, a ring, and a plate. The means for mixing can be fully inside a sample container, for example a battery-powered propeller. Alternatively, the means for mixing can be partially inside a sample container and partially outside a sample container, for example a magnetic stir bar can be inside the sample container and a magnetic field device can be outside the sample container. In embodiments where part of the means for mixing is outside the sample container, it is preferred that it be a part of a sample processing instrument.

A sample to be inserted into a sample container can be solid, for example a head of lettuce, or can be liquid, for example urine or blood, or a combination thereof. A solid (or substantially solid) sample will need to be at least partially homogenized (converted at least partially into a fluid) so that it can be transported to, prepared by, and transported out of the sample preparation cartridge, and the at least partial homogenization can occur inside the sample container, outside the sample container, or both. A sample can be (at least partially) homogenized using any suitable means including but not limited to biological liquefaction using, for example, a microorganism or enzyme, chemical liquefaction using, for example, an acid or base, or mechanical liquefaction, using, for example, a paddle blender (stomacher). A sample can be a food matrix, for example meat or produce, and/or it can be an environmental sample, for example a swab or sponge. A sample can be any size that fits in a sample container but preferably the sample weighs between 5 g and 350 g.

A sample container can also comprise a semipermeable membrane. A sample in a sample container can be a mix of fluid and particulates, so a semipermeable membrane can be used to separate substances in the sample using size exclusion. The semipermeable membrane should be designed to allow at least some of the substances of interest in the sample to cross the membrane. Advantages of using a semipermeable membrane include but are not limited to reducing the viscosity of a sample and removing particulates that can prevent or impede the sample preparation process. A semipermeable membrane is used to partition the sample container into a first sample section and a second sample section. The sample can be loaded into the first sample section through at least one sample container port in fluidic connectivity with the first sample section. At least some of the substances in the sample are able to cross the semipermeable membrane and enter the second sample section. The second sample section is in fluidic connectivity with the lysis chamber of at least one sample preparation cartridge.

The process of at least some substances in the sample crossing the semipermeable membrane can be aided by employing a means for mixing in the sample container as described above. The sample mixing can occur in the first sample section, the second sample section, or both sample sections. For example, a sample container can comprise two magnetic stir bars, one in the first sample section and one in the second sample section, and the stir bars can be controlled using at least one magnetic field device on the sample preparation cartridge or on a sample processing instrument.

A sample container can also comprise a media for growing organisms in a sample. Examples of media for growing organisms, for example *Salmonella* species, in a sample include but are not limited to Rappaport-Vassiliadis (RV) medium and tetrathionate (TT) broth. To affect the growth of organisms in a sample, antimicrobial compounds and/or other additives can be added to the sample and/or media. Examples of antimicrobial compounds include but are not limited to acriflavine, nalidixic acid, cycloheximide, novobiocin, cefsulodin, and vancomycin. Examples of other additives include but are not limited to morpholinepopanesulfonic acid (MOPS), casamino acids, yeast extract, and sodium pyruvate (Bacteriological Analytical Manual).

A sample container should maintain a sample at a temperature between 30° C. and 45° C., preferably between 35° C. and 42° C.

Metering of Fluids

An advantage of the sample preparation cartridge is that it allows for precise metering of fluids. For example, a sample preparation cartridge (in fluidic connectivity with a sample, at least one fluidic movement source, and optionally a valve) is capable of flowing between 10 μL and 10,000 μL of the sample, preferably between 100 μL and 1000 μL of the sample, to the sample preparation cartridge. For a second example, a sample preparation cartridge is capable of flowing between 10 μL and 10,000 μL of a lysis buffer, preferably between 100 μL and 1000 μL of a lysis buffer, to the sample preparation cartridge. For a third example, a sample preparation cartridge is capable of flowing between 10 μL and 10,000 μL of a wash buffer, preferably between 100 and 1000 μL of a wash buffer, to the sample preparation cartridge. For a fourth example, a sample preparation cartridge is capable of flowing between 10 μL and 1000 μL of an elution buffer, preferably between 20 μL and 200 μL of an elution buffer, to the sample preparation cartridge.

The fluidics of the invention allow for precision metering of fluids. For example, a high-precision fluidic movement source, such as a high-precision syringe pump, (in fluidic connectivity with a sample preparation cartridge) can precisely and accurately control the flow rates and volumes into, out of, and through a sample preparation cartridge. Metering of fluids avoids the need for users to measure and add a specific volume of sample for processing and thereby can reduce sample workflow times and user errors.

Sample Processing Instrument

A sample preparation cartridge can be used in conjunction with a sample processing instrument, such as a sample identification instrument. A sample identification instrument can use any means of identifying the nucleic acids in a sample including but not limited to polymerase chain reaction (PCR), fluorescence in situ hybridization (FISH), arrays, and sequencing. The sample preparation cartridge provides an upstream means for preparing a sample for downstream sample processing by a sample processing instrument.

A sample preparation cartridge can be designed to be in fluidic connectivity with a sample processing instrument. The sample processing instrument can be designed to be in fluidic connectivity with a sample preparation cartridge before, during, and/or after sample preparation (i.e., before, during, and/or after the sample undergoes lysis and nucleic acid capture, and optionally selective capture). Any sample preparation method that requires external components, for example an outside magnetic field device, is preferably incorporated into the sample processing instrument. The sample preparation cartridge and sample processing instrument are designed to allow for operable connectivity between the external sample processing components and the internal sample processing components and/or the sample. For example, an external heating device incorporated into a sample processing instrument needs to be in thermal connectivity with a sample to lyse the sample using heat. For an additional example, an external magnetic field device incorporated into a sample processing instrument needs to be in magnetic connectivity with magnetic beads in the lysis chamber to lyse the sample using mechanical lysis. External sample preparation components that are preferably incorporated into a sample processing instrument include but are not limited to a heating device, a magnetic field device, and an acoustic wave device.

A sample preparation apparatus comprising a sample preparation cartridge and a sample container can be designed to be in fluidic connectivity with a sample processing instrument. The sample processing instrument can be designed to be in fluidic connectivity with a sample preparation cartridge (which is in fluidic connectivity with a sample container) before, during, and/or after sample preparation (i.e., before, during, and/or after the sample undergoes lysis and nucleic acid capture, and optionally selective capture). Any sample processing that requires external components, for example an outside magnetic field device, is preferably incorporated into the sample processing instrument. The sample preparation cartridge, sample container, and sample processing instrument are designed to allow for operable connectivity between the external sample processing components and the internal sample processing components and/or the sample. For example, an external heating device incorporated into a sample processing instrument needs to be in thermal connectivity with a sample to lyse the sample using heat. For an additional example, an external magnetic field device incorporated into a sample processing instrument needs to be in magnetic connectivity with magnetic beads in the lysis chamber to lyse the sample using mechanical lysis. External components for at least partially homogenizing a sample in a sample container are preferably incorporated into a sample processing instrument. For example, a sample to be at least partially homogenized by paddle blending can be in a flexible sample container, for example a bag, and the paddles for paddle blending can be incorporated in the sample processing instrument. External sample preparation components (including external components for treating a sample in a sample container prior to introduction into a sample preparation cartridge) that are preferably incorporated into a sample processing instrument include but are not limited to a heating device, a magnetic field device, an acoustic wave device, and a mechanical homogenizing device.

Multiple Sample Preparation Cartridges

Multiple sample preparation cartridges can be used with a sample. A preferred embodiment is at least two sample preparation cartridges in fluidic connectivity with a sample container. An advantage of using at least two sample preparation cartridges in fluidic connectivity with a sample container is that a sample in a sample container can be prepared and processed at different time points. For example, three sample preparation cartridges can be in fluidic connectivity with a sample container. A sample can be inserted into the sample container and allowed to grow. The first sample preparation cartridge can prepare a portion of (sample of) the sample at a first time point (t1), the second sample preparation cartridge can prepare a portion of the sample at a second time point (t2), and the third sample preparation cartridge can prepare a portion of the sample at a third time point (t3). Each of the three portions of the sample can be processed by a sample processing instrument, for example a sample detection instrument. One advantage of processing a sample at multiple time points is the ability to determine whether an organism present in the sample is viable or non-viable. For example, for certain samples tested for pathogenic contaminants, such as food and food products that undergo a kill step during processing, a significant increase in target signal between testings at the initial time point and subsequent time point(s) indicates the presence of live pathogens in the sample that survived the kill step. On the contrary, the absence of a significant increase in target signal between testings at the initial time point and subsequent time point(s), indicates that the original signal could have come from nucleic acids present in the sample from dead organisms that were inactivated during the kill step. The time series interval typically ranges from a period of 15 minutes to 10 hours, preferably 1 hour to 4 hours.

REFERENCES

The list of references below may not be exhaustive and other references may be found throughout specification.
U.S. Pat. No. 9,096,823
U.S. Patent Application No. 2006/0115873
PCT Patent Application No. PCT/US2020/029199
PCT Patent Application No. PCT/US2020/034179
Bacteriological Analytical Manual, 8th Edition, Revision A, 1998.
Herzer, S. (2001). "DNA Purification" in Gerstein, A. S. (ed.) Molecular Biology Problem Solver: A Laboratory Guide. Wiley, pp. 167-195.
Tu, S. I., Reed, S., Gehring, A., He, Y., Paoli, G. Capture of *Escherichia coli* O157:H7 Using Immunomagnetic Beads of Different Size and Antibody Conjugating Chemistry. Sensors (Basel). 2009; 9(2):717-30.

What is claimed is:

1. A sample preparation cartridge, comprising:
   a lysis chamber, comprising:
      a filter partitioning the lysis chamber into a first lysis chamber section and a second lysis chamber section;
      a first lysis chamber port in fluidic connectivity with the first lysis chamber section;
      a second lysis chamber port in fluidic connectivity with the first lysis chamber section; and
      a means for lysing; and
   a nucleic acid capture chamber, comprising:
      a fluidic channel with an inlet and an outlet, wherein the inlet is in fluidic connectivity with the second lysis chamber section;
      a nucleic acid capture chamber port in fluidic connectivity with the outlet of the fluidic channel; and
      a nucleic acid binding unit in the fluidic channel; and
   wherein the first lysis chamber port is capable of establishing fluidic connectivity with a fluid comprising nucleic acids, the second lysis chamber port is capable of establishing fluidic connectivity with at least one fluidic movement source capable of flowing the fluid to the first lysis chamber section, the nucleic acid capture chamber port is capable of establishing fluidic connectivity with at least one fluidic movement source capable of flowing the fluid in the second lysis chamber section through the fluidic channel.

2. The sample preparation cartridge of claim 1, wherein the means for lysing is in the first lysis chamber section.

3. The sample preparation cartridge of claim 1, wherein the means for lysing is at least one moveable structure.

4. The sample preparation cartridge of claim 1, wherein the at least one moveable structure is magnetic.

5. The sample preparation cartridge of claim 3, wherein the at least one moveable structure is selected from the group consisting of a bar, a bead, a ring, a plate, and a combination thereof.

6. The sample preparation cartridge of claim 1, wherein the means for lysing is selected from the group consisting of a heating device, an acoustic wave device, a mixing device, and a combination thereof.

7. The sample preparation cartridge of claim 1, wherein the means for lysing is selected from the group consisting of an enzyme, a chemical, and a combination thereof.

8. The sample preparation cartridge of claim 1, wherein the lysis chamber further comprises a means for selectively capturing at least one substance in the fluid.

9. The sample preparation cartridge of claim 8, wherein the means for selectively capturing is in the first lysis chamber section.

10. The sample preparation cartridge of claim 8, wherein the means for selectively capturing is selected from the group consisting of a ligand, a functionalized surface, and a combination thereof.

11. The sample preparation cartridge of claim 10, wherein the ligand is selected from the group consisting of an antibody, an aptamer, a polysaccharide, a protein, and a combination thereof.

12. The sample preparation cartridge of claim 1, wherein the first lysis chamber port is in fluidic connectivity with a sample container.

13. The sample preparation cartridge of claim 1, wherein the nucleic acid binding unit is selected from the group consisting of a frit, a filter, a membrane, and a combination thereof.

14. The sample preparation cartridge of claim 1, wherein the first lysis chamber port is in fluidic connectivity with a fluid comprising nucleic acids, the second lysis chamber port is in fluidic connectivity with at least one fluidic movement source, and the nucleic acid capture chamber port is in fluidic connectivity with at least one fluidic movement source.

15. The sample preparation cartridge of claim 14, wherein the at least one fluidic movement source is capable of flowing between 10 µL and 10,000 µL of the fluid to the first lysis chamber section.

16. A sample preparation cartridge, comprising:
   a lysis chamber, comprising:
      a filter partitioning the lysis chamber into a first lysis chamber section and a second lysis chamber section;
      a first lysis chamber port in fluidic connectivity with the first lysis chamber section;
      a second lysis chamber port in fluidic connectivity with the first lysis chamber section;
      a third lysis chamber port in fluidic connectivity with the second lysis chamber section; and
      a means for lysing; and
   a nucleic acid capture chamber, comprising:
      a fluidic channel with an inlet and an outlet, wherein the inlet is in fluidic connectivity with the second lysis chamber section;
      a nucleic acid capture chamber port in fluidic connectivity with the outlet of the fluidic channel; and
      a nucleic acid binding unit in the fluidic channel; and
   wherein the first lysis chamber port is capable of establishing fluidic connectivity with a fluid comprising nucleic acids, the second lysis chamber port is capable of establishing fluidic connectivity with at least one fluidic movement source capable of flowing the fluid to the first lysis chamber section, the third lysis chamber port is capable of establishing fluidic connectivity with at least one fluidic movement source capable of flowing the fluid from the second lysis chamber section, and the nucleic acid capture chamber port is capable of establishing fluidic connectivity with at least one fluidic movement source capable of flowing the fluid in the second lysis chamber section through the fluidic channel.

17. A sample preparation apparatus, comprising:
a sample preparation cartridge, comprising:
   a lysis chamber, comprising:
      a filter partitioning the lysis chamber into a first lysis chamber section and a second lysis chamber section;
      a first lysis chamber port in fluidic connectivity with the first lysis chamber section;
      a second lysis chamber port in fluidic connectivity with the first lysis chamber section;
      a third lysis chamber port in fluidic connectivity with the second lysis chamber section; and
      a means for lysing;
   a nucleic acid capture chamber, comprising:
      a fluidic channel with an inlet and an outlet, wherein the inlet is in fluidic connectivity with the second lysis chamber section;
      a nucleic acid capture chamber port in fluidic connectivity with the outlet of the fluidic channel; and
      a nucleic acid binding unit in the fluidic channel; and
   a sample container, comprising:
      at least one sample container port; and
   wherein the first lysis chamber port is in fluidic connectivity with the at least one sample container port, the second lysis chamber port is capable of establishing fluidic connectivity with at least one fluidic movement source capable of flowing fluid comprising nucleic acids in the sample container to the first lysis chamber section, the third lysis chamber port is capable of establishing fluidic connectivity with at least one fluidic movement source capable of flowing the fluid from the second lysis chamber section, and the nucleic acid capture chamber port is capable of establishing fluidic connectivity with at least one fluidic movement source capable of flowing the fluid in the second lysis chamber section through the fluidic channel.

18. A sample preparation apparatus, comprising:
at least two sample preparation cartridges, each comprising:
   a lysis chamber, comprising:
      a filter partitioning the lysis chamber into a first lysis chamber section and a second lysis chamber section;
      a first lysis chamber port in fluidic connectivity with the first lysis chamber section;
      a second lysis chamber port in fluidic connectivity with the first lysis chamber section;
      a third lysis chamber port in fluidic connectivity with the second lysis chamber section; and
      a means for lysing;
   a nucleic acid capture chamber, comprising:
      a fluidic channel with an inlet and an outlet, wherein the inlet is in fluidic connectivity with the second lysis chamber section;
      a nucleic acid capture chamber port in fluidic connectivity with the outlet of the fluidic channel; and
      a nucleic acid binding unit in the fluidic channel; and
a sample container, comprising:
   at least one sample container port; and
wherein for each sample preparation cartridge:
   the first lysis chamber port is in fluidic connectivity with the at least one sample container port;
   the second lysis chamber port is capable of establishing fluidic connectivity with at least one fluidic movement source capable of flowing fluid comprising nucleic acids in the sample container to the first lysis chamber section;
   the third lysis chamber port is capable of establishing fluidic connectivity with at least one fluidic movement source capable of flowing the fluid from the second lysis chamber section; and
   the nucleic acid capture chamber port is capable of establishing fluidic connectivity with at least one fluidic movement source capable of flowing the fluid in the second lysis chamber section through the fluidic channel.

* * * * *